United States Patent [19]
Lockhoff et al.

[11] Patent Number: 5,905,071
[45] Date of Patent: May 18, 1999

[54] GLYCOSYLAMIDES OF 2-AMINOACYLAMINO-2-DEOXY SUGARS

[75] Inventors: Oswald Lockhoff; Burkhard Mielke, both of Leverkusen; Helmut Brunner; Klaus Schaller, both of Wuppertal, all of Germany

[73] Assignee: Bayer Aktiengesellschaft, Leverkusen, Germany

[21] Appl. No.: 08/605,031

[22] PCT Filed: Aug. 17, 1994

[86] PCT No.: PCT/EP94/02736

§ 371 Date: Jun. 25, 1996

§ 102(e) Date: Jun. 25, 1996

[87] PCT Pub. No.: WO95/06654

PCT Pub. Date: Mar. 9, 1995

[30] Foreign Application Priority Data

Aug. 30, 1993 [DE] Germany .............................. 43 29 095
Feb. 11, 1994 [DE] Germany .............................. 44 04 371

[51] Int. Cl.[6] .......................... A61K 31/70; A01N 43/04; C07H 15/00
[52] U.S. Cl. ................................. 514/62; 514/2; 514/23; 514/25; 514/43; 514/885; 536/4.1; 536/17.2; 536/17.3; 536/17.4; 536/17.7; 536/18.5; 536/18.6; 536/18.7; 536/53; 536/116; 536/122; 536/123
[58] Field of Search ..................................... 536/4.1, 17.2, 536/17.4, 17.3, 17.7, 18.6, 18.5, 18.7, 53, 116, 122, 123; 514/23, 25, 43, 45, 46, 49, 50, 62, 885, 2

[56] References Cited

U.S. PATENT DOCUMENTS 4,308,376 12/1981 Lemieux et al. ........................ 536/18.7
4,362,720 12/1982 Lemieux et al. ........................ 536/18.7
4,683,222 7/1987 Stradler et al. .
4,855,283 8/1989 Lockhoff et al. .

FOREIGN PATENT DOCUMENTS 0091645 10/1983 European Pat. Off. .
0338308 10/1989 European Pat. Off. .

OTHER PUBLICATIONS

O. Lockhoff et al., Angewandte Chemie International Ed. Eng. vol. 30,pp.1611–1620 (1991).
A. Hubbuch, Kontakte, No. 3, pp. 19–22 (1979).
E.E. Bullesbach, Kontakte, No. 1,pp. 23–35 (1980).
E.Wunsch, in. "Methoden Der Organischen Chemie (Houben–Wegl)", E. Muller, ed., vol. XV/1 and XV/II, 4th ed., thiene Veilog, Stuffgart (1974).

*Primary Examiner*—James O. Wilson
*Attorney, Agent, or Firm*—Sprung Kramer Schaefer & Briscoe

[57] ABSTRACT

The present invention relates to (2-aminoacylamino-2-deoxy-glycosyl)-amides, which are substituted on the nitrogen atom of the amino acid, of the general formula (I)

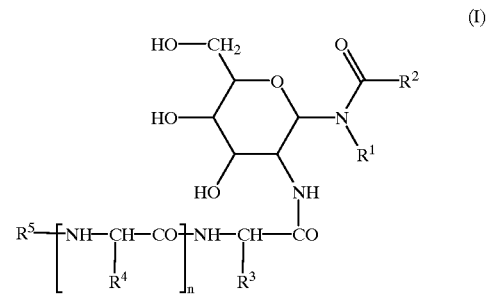

in which the substituents have the meaning given in the description, to processes for their preparation and to their use in medicaments.

10 Claims, No Drawings

GLYCOSYLAMIDES OF 2-AMINOACYLAMINO-2-DEOXY SUGARS

The invention relates to (2-anmioacylamino-2-deoxy-glycosyl)-amides which are substituted on the nitrogen atom, to processes for their preparation, and their use in medicaments.

It is known that glycosylamides of aldopyranoses or of amino sugars are able to intensify the endogenous immune response (DE-A 32 13 650). It is also known that (2-amino-2-deoxy-glycosyl)-amides substituted with amino acids can bring about an increase both in the specific and in the nonspecific immune response (DE-A 35 21 994).

Now, the present invention relates to (2-aminoacylamino-2-deoxy-glycosyl)-amides which are substituted on the nitrogen atom of the amino acid, of the general formula (I)

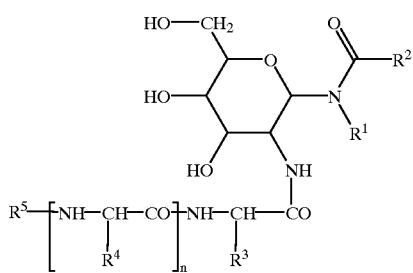

(I)

in which
- $R^1$ represents straight-chain or branched, saturated or unsaturated alkyl having up to 25 carbon atoms,
- $R^2$ represents straight-chain or branched, saturated or unsaturated allyl having up to 25 carbon atoms,
- $R^3$ represents hydrogen, $C_1$- to $C_7$-alkyl, hydroxy-methyl, 1-hydroxy-ethyl, mercapto-methyl, 2-methylthio-ethyl, 3-amino-propyl, 3-ureido-propyl, 3-guanidyl-propyl, 4amino-butyl, carboxy-methyl, carbamoyl-methyl, 2-carboxy-ethyl, 2-carbamoyl-ethyl, benzyl, 4-hydroxy-benzyl, 3-indolyl-methyl or 4-imidazolyl-methyl,
- $R^4$ has the above-indicated meaning of $R^3$ and is identical to or different from it,
- $R^5$ represents hydrogen or a protecting group which is custorary in peptide chemistry (cf. A Hubbuch, Kontakte (Darmstadt) 1979, 14; E. E. Bullesbach, Kontakte (Darmstadt) 1980, 23), and in which
n denotes a number 1, 2 or 3,
and in the case where n=2 or 3 the individual meanings of $R_4$ can be different.

The compounds according to the invention have a plurality of asymmetric carbon atoms. They can therefore exist in different stereochemical forms. The invention relates both to the individual isomers and to mix thereof.

Preferred compounds of the general formula (I) are those in which
- $R^1$ represents a straight-chain, saturated or monounsaturated alkyl radical having 10 to 20 carbon atoms,
- $R^2$ represents a straight-chain, saturated or monounsaturated alkyl radical having 10 to 20 carbon atoms,
- $R^3$ represents hydrogen, $C_1$- to $C_7$-alkyl, hydroxy-methyl, 1-hydroxy-ethyl, mercapto-methyl, 2-methylthio-ethyl, 3-amino-propyl, 3-ureido-propyl, 3-guanidyl-propyl, 4-amino-butyl, carboxy-methyl, carbamoyl-methyl, 2-carboxy-ethyl, 2-carbamoyl-ethyl, benzyl, 4hydroxy-benzyl, 3-indolyl-methyl or 4-imidazolyl-methyl,
- $R^4$ has the above-indicated meaning of $R^3$ and is identical to or different from it,
- $R^5$ represents hydrogen, acetyl, benzoyl, trichloroacetyl, trifluoroacetyl, methoxycarbonyl, tert-butyloxycarbonyl, allyloxycarbonyl, trichloroethoxycarbonyl, benzyloxycarbonyl or fluorenylmethoxycarbonyl, and in which
n denotes a number 1, 2 or 3,
and in the case where n=2 or 3 the individual meanings of $R_4$ can be different.

In addition, two processes have been found for the preparation of the compounds of the general formula (I) according to the invention. The two processes differ in the sequence and in the structural units with which the peptide linkages can be linked.

In the first process (A), N-(2-aminoacylamino-2-deoxy-hexopyranosyl)-N-alkyl-carboxamides of the formula (II)

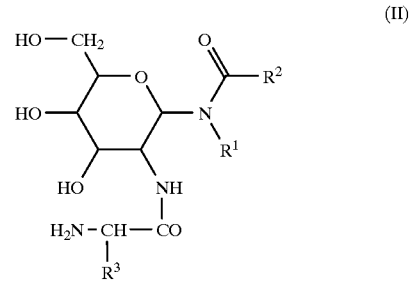

(II)

in which
$R^1$, $R^2$ and $R^3$ have the meaning given above
are reacted with amino acid derivatives or di- or tripeptide derivatives of the general formula (III)

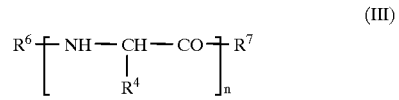

(III)

in which
- $R^4$ has the meaning given above,
- $R^6$ represents a protecting group, customary in peptide chemistry, for the nitrogen atom of amino acids, which can be eliminated again selectively to give the peptide linkage, and
- $R^7$ represents a hydroxyl group or a leaving group, customary in peptide chemistry, for the activation of amino acids,
- n denotes a number 1, 2 or 3,
- and in the case where n is 2 or 3 the individual meanings of $R^4$ can be different, with one another in such a way that an amide linkage is formed and compounds of the general formula (I) are obtained.

In a second reaction step, the N-terminal protecting group $R^5$ in the compounds of the formula (I) is eliminated to give the compounds of the general formula (I) having a free amino group.

The starting compounds of the general formula (II) are known and can be prepared by the methods described in DE 3521994 (Le A 23620).

The derivatives of the di- or tripeptides of the general formula (III) are likewise known in principle.

Examples of suitable protecting groups $R^6$ for the amino function in compounds of the formula (III) are acyl groups such as trifluoroacetyl or trichloroacetyl, o-nitrophenylsulphenyl, 2,4-dinitrophenylsulphenyl or optionally substituted lower alkoxycarbonyl, for example methoxycarbonyl, tert-butyloxycarbonyl, benzyloxycatbonyl, p-methoxybenzyloxycarbonyl, fluorenylmethoxycarbonyl or 2,2,2-trichloroethoxycarbonyl.

Preferred amino-protecting groups $R^6$ are the tert-butyloxycarbonyl group or the benzyloxycarbonyl group.

The linkage of the 2-aminoacylamino-2-deoxyglycosylamides of the general formula (II) with the N-substituted amino acids, di- or tripeptides of the general formula (III) can be accomplished by conventional methods of peptide chemistry (E. Wünsch et al.: Synthese von Peptiden [Synthesis of Peptides] in: Methoden der Organischen Chemie [Methods of Organic Chemistry] (Houben-Weyl) (E. Muller, ed.) Volume XV/I and XV/II, 4th ed., Thieme Verlag Stuttgart (1974)).

Conventional methods are, for example, the condensation of the amino function in the compound of the general formula (II) with an N-protected amino-acid or peptide derivative of the general formula (III) in the presence of dehydrating agents, for example carbodiimides such as dicyclohexylcarbodiimide or diisopropylcarbodiimide.

The condensation of the compounds of the formula (II) with the compounds of the formula (III) can also be carried out if the carboxyl group is activated. An activated carboxyl group can, for example, be a carboxylic anhydride, preferably a mixed anhydride with alkyl carbonates, acetic acid or another carboxylic acid, or an amide of the acid, such as an imidazolide, or an activated ester, for example the cyanomethyl ester, pentachlorophenyl ester or N-hydroxyphthalimide ester. Activated esters can also be obtained from the amino-acid derivatives of the formula (III) in which $R^7$ represents OH, and N-hydroxysuccinimide or 1-hydroxybenzotriazole in the presence of a dehydrating agent such as carbodiimide.

In the second process step for the preparation of the compounds of the general formula (I), the protecting group $R^5$ is eliminated.

The protecting groups $R^5$ which are preferably used in the compounds of the general formula (I), the N-carbobenzoxy group and the N-tert-butyloxycarbonyl group, can be eliminated to give the amide groups which exist in the compounds. Methods of this type are known in principle.

The carbobenzoxy group in the compounds of the formula (I) can be selectively eliminated by hydrogenolysis in the presence of transition metals, for example palladium on carbon, in a suitable solvent such as, for example, methanol, ethanol, glacial acetic acid or tetrahydrofuran, either in pure form or in a combination of the solvents with one another, or alternatively with water, it being possible to operate both at atmospheric pressure and at elevated pressure.

The tert-butoxycarbonyl group in the compounds of the formula (I) can be eliminated by means of acidolytic processes. Examples of suitable conditions are the use of hydrogen chloride or trifluoroacetic acid, either in pure form or diluted in suitable solvents such as, for example, glacial acetic acid, dichloromethane, diethyl ether, dioxane or ethyl acetate.

The compounds of the general formula (I) obtained in this way are isolated, by methods which are known per se, in the form of crystalline or amorphous solids and are purified if necessary by recrystallization, chromatography, extraction, etc.

In the second process (B), the compounds of the formula (I) according to the invention are obtained by linking N-(2-amino-2deoxy-hexopyranosyl)-N-alkyl-carboxamides with di-, tri- or tetrapepide derivatives.

Process (B) is characterized in a compounds of the general formula (IV)

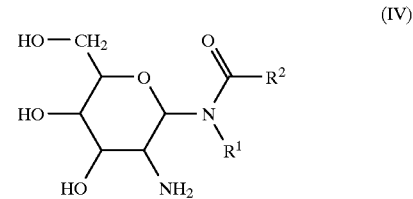

(IV)

in which
$R^1$ and $R^2$ have the meaning given above
are reacted with derivatives of di-, tri- or teptides of the general formula (III)

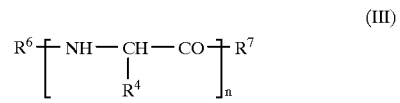

(III)

in which
$R^4$ and $R^7$ have the meaning given above and
$R^6$ denotes a protecting group
and in which
n denotes a number 2, 3 or 4 with one another under the abovementioned conditions with formation of a peptide linkage, to give the compounds of the formula (V)

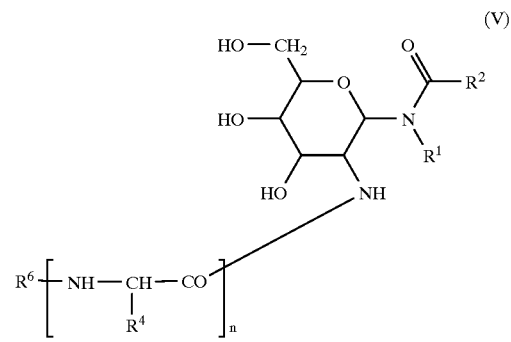

(V)

in which $R^1$, $R^2$, $R^4$ and $R^6$ have the meanings given above and
n denotes a number 2, 3 or 4,
which are substituted on the N-terminal amino group.

Subsequently, in the substituted compounds of the formula (V), the amino-protecting groups $R^6$ must be eliminated to give compounds having an unsubstituted amino group, of the general formula (I).

The preparation of the starting compounds of the formula (IV) is described in DE 3521994 (Le A 23620). For the conditions of the linking of the peptide linkages, the general methods of peptide synthesis indicated above can be employed.

Also part of the invention are salts of the compounds of the formula (I). These are primarily customary, pharmaceutically utilizable, nontoxic salts, for example the ammonium salts of chlorides, acetates, lactates.

It has been found that the compounds of the general formula (I) identified more closely below bring about a stimulation of and therefore an improvement in endogenous defence processes. The compounds can therefore be used as immunologically active medicaments. The immunostimulating effect has been demonstrated both in vivo in animal experimentation and in vitro on cells of the defence system. This fact is evidenced by the following experimental results.

Female mice ($CFW_1$) weighing about 18 g were divided into groups on the basis of random criteria. The animals were then administered, intraperitoneally, subcutaneously or intravenously, a dose of 10 mg/kg of body weight of the compounds of the formula (I) according to the invention, or received physiological saline solution. Twenty-four hours later, the animals were injected intraperitoneally with 10 times the lethal dose ($LD_{50}$) of *Escherichia coli* C14. The table which follows shows that the survival rates seven days after infection in mice which had been treated with the compounds of the formula (I) according to the invention was significantly greater than that of mice having received physiological saline solution.

TABLE

| Example | Surviving mice on day 7 p.i. (difference relative to control) | p* |
| --- | --- | --- |
| 22a | 7/16 (44%) | <0.05 |
| 22b | 7/16 (44%) | <0.05 |
| 22c | 9/16 (56%) | <0.01 |
| 22d | 12/16 (75%) | <0.001 |
| 22e | 9/16 (56%) | <0.01 |
| 22h | 10/16 (63%) | <0.001 |
| 22k | 11/16 (69%) | <0.001 |
| 25f | 4/12 (33%) | |
| 26a | 10/16 (63%) | <0.001 |
| 26b | 11/16 (69%) | <0.001 |
| 26c | 9/16 (56%) | <0.01 |
| 26d | 7/16 (44%) | <0.05 |
| 26e | 11/16 (69%) | <0.001 |
| 26f | 7/16 (44%) | <0.05 |
| 26g | 10/16 (63%) | <0.001 |
| 26h | 9/16 (56%) | <0.01 |
| 26i | 14/16 (88%) | <0.001 |
| 26j | 11/16 (69%) | <0.001 |
| 26k | 10/16 (63%) | <0.001 |
| 27c | 4/16 (25%) | |
| 27d | 12/16 (75%) | <0.001 |
| 27e | 7/16 (44%) | <0.05 |
| 27h | 8/16 (50%) | <0.01 |
| 27i | 7/16 (44%) | <0.05 |
| 27j | 8/16 (50%) | <0.01 |

*Fisher test
p.i. = post-infection

Protective screening in the neutropenic Candida infection model

The aim of this experimental model is to discover substances which stimulate endogenous defence in neutropenic mice.

Methodology

At time −96 h, the mice are treated intraperitoneally with 0.2 ml of Endoxan in a dose of 200 mg/kg per animal. At the times −72, −48 and −24 h, the mice are treated intraperitoneally with 0.2 ml of the solution of the screening substance. Alternatively, treatments with screening substances are also carried out with 0.2 ml of solution subcutaneously and intravenously, and with 0.5 ml of solution orally. 2 groups each containing 10 animals are used per preparation. Routinely, one group is treated with 10 mg/kg, the other with 30 mg/kg, of body weight. For in-depth examinations, substantially lower dosages are also used.

At time 0 h, the mice are infected intravenously with 0.2 ml of a lethal pathogen suspension into the caudate vein.

Observation and Assessment

The mice are observed up to 4 h after treatment in order to enable detection of any instances of incompatibility with the preparation.

From 1 day to 14 days after infection, the mice are assessed once daily before midday. The state of health is registered in 5 grades.
(-good-slightly ill-ill-severely ill-dead-)
The severely ill mice are killed after evaluation so as not to suffer.

Result

The result documented is the survival ratio and/or retardation of the clinical picture. In both cases this is done in comparison with the control mice treated with Endoxan.

Techniques

Intraperitoneal, subcutaneous and intravenous administrations were carried out by us using a 1 ml disposable syringe and a No. 18 syringe. Oral administration is carried out with a 5 ml disposable syringe and the No. 12 syringe with olive. For intraperitoneal and oral administration, the mice are fixed in the hand. In the case of subcutaneous administration, the mice are fixed on the cage lid. In the case of intravenous administration and intravenous infection, the mice are fixed in a mouse enforcement cage. In addition, prior to intravenous treatment and intravenous infection the mice are placed for about 10 minutes under red light in order to widen the caudate veins.

Parameters

| | |
| --- | --- |
| Mouse: | $B_6D_2F_1$ 20 g, female |
| Pathogen: | Candida albicans, $5 \times 10^5$ microbes per mouse |
| Substance: | Endoxan is water-soluble. The screening substances, if possible, are likewise dissolved in sterile water. Where this is not possible, an attempt is made to dissolve them as follows: initial dissolution in pure DMSO (final concentration of DMSO in the solution for administration = 2%). Cremophor was then added (final concentration of Cremophor in the solution for administration = 8%). The composition is made up with sterile water to the final volume. |
| Living conditions: | The animals are kept in type II Makrolon cages. All animals receive feed and water ad libitum. |

The compound from Example 22 h shows a good protective effect in the Candida infection model.

PREPARATION EXAMPLES

Example 1

General procedure for reacting the 2-amino-2-deoxy compounds of the formula (IV) and the 2-aminoacylamino-2-deoxy compounds of the formula (II) with N-protected amino acids, di- or tripeptides of the general formula (III) to give the N-protected 2-aminoacylamino-2-deoxy compounds, substituted with amino acids, of the formula (I):

N,N'-Dicyclohexylcarbodiimide (1.88 g, 8.4 mmol) is added to a mixture of the N-protected α-amino acid or, respectively, of the di- or oligopeptide (7.7 mmol), N-hydroxysuccinimide (1.77 g, 15.4 mmol) and N,N-dimethylformamide (70 ml), and the mixture is stirred at 20° for 30 min. Ethyl-diisopropylamine (8.0 mmol) and the 6-amino-6-deoxy compound of Example II (7.0 mmol) are added, and stirring is continued for 16 h. Water (3 ml) is added to the mixture, stirring is continued for 30 minutes, and the mixture is concentrated under reduced pressure to a syrup. The residue is stirred with diethyl ether (100 ml), the precipitated urea is filtered off with suction, and the filtrate is concentrated under a high vacuum. The residue is taken up in diethyl ether (150 ml), washed three times with water (70 ml each time), dried over magnesium sulphate and concentrated under reduced pressure to a syrup. The residue is filtered over silica gel (eluent dichloromethane/methanol/conc. ammonia water 25:1:0.05).

11a N-[2-(N-Carbobenzoxy-glycyl-glycyl)-amino-2-deoxy-β-D-glucopyranosyl]-N-dodecyl-dodecanamide.
   from N-(2-glycyl-amino-2-deoxy-β-D-glucopyranosyl)-N-dodecyl-dodecanamide and N-carbobenzoxy-glycine.

11b N-[2-(N-Carbobenzoxy-L-alanyl-glycyl)-amino-2-β-D-glucopyranosyl]-N-dodecyl-dodecanamide.
   from N-(2-glycyl-amino-2-deoxy-β-D-glucopyranosyl)-N-dodecyl-dodecanamide and N-carbobenzoxy-L-alanine.

11c N-[2-(N-Carbobenzoxy-L-phenylalanyl-glycyl)-amino-2-deoxy-β-D-glucopyranosyl]-N-dodecyl-dodecanamide.
   from N-(2-glycyl-amino-2-deoxy-β-D-glucopyranosyl)-N-dodecyl-dodecanamide and N-carbobenzoxy-L-phenylalanine Yield 53%. $R_f$ 0.29 (dochloromethane/methanol/conc. ammonia 15:1:0.1).

11d N-[2-(N-Carbobenzoxy-glycyl-L-alanyl)-amino-2-deoxy-β-D-glucopyranosyl]-N-dodecyl-dodecanamide.
   from N-(2-L-alanyl-amino-2-deoxy-β-D-glucopyranosyl)-N-dodecyl-dodecanamide and N-carbobenzoxy-glycine.

11e N-[2-(N-Carbobenzoxy-glycyl-D-alanyl)-amino-2-deoxy-β-D-glucopyranosyl]-N-dodecyl-dodecanamide.
   from N-(2-D-alanyl-amino-2-deoxy-β-D-glucopyranosyl)-N-dodecyl-dodecanamide and N-carbobenzoxy-glycine.

11f N-[2-(N-Carbobenzoxy-4-O-benzyl-L-aspartyl-D-alanyl)-amino-2-deoxy-β-D-glucopyranosyl]-N-dodecyl-dodecanamide.
   from N-(2-D-alanyl-amino-2-deoxyl-β-D-glucopyranosyl)-N-dodecyl-dodecanamide and N-carbobenzoxy-4-O-benzyl-L-aspartic acid. Yield 63%. $R_f$ 0.57 (dichloromethane/methanol/conc. ammonia 15:1:0.1).

12a N-[2-(N-Carbobenzoxy-glycyl-glycyl)-amino-2-deoxy-β-D-glucopyranosyl]N-tetradecyl-dodecanamide.
   from N-(2-glycyl-amino-2-deoxy-β-D-glucopyranosyl)-N-tetradecyl-dodecanamide and N-carbobenzoxy-glycine. Yield 47%. $[\alpha]_D=+18.7°$ (c=0.95, dichloromethane). m.p. 108–109°.

12b N-[2-(N-Carbobenzoxy-sarcosyl-glycyl)-amino-2-deoxy-β-D-glucopyranosyl]-N-tetradecyl-dodecanamide.
   from N-(2-glycyl-amino-2-deoxy-β-D-glucopyranosyl)-N-tetradecyl-dodecanamide and N-carbobenzoxy-sarcosine. Yield 64%. $[\alpha]_D=+18.4°$ (c=1.02, dichloromethane). m.p. 76–77°.

12c N-[2-(N-Carbobenzoxy-L-alanyl-glycyl)-amino-2-deoxy-β-D-glucopyranosyl]-N-tetradecyl-dodecanamide.
   from N-(2-glycyl-amino-2-deoxy-β-D-glucopyranosyl)-N-tetradecyl-dodecanamide and N-carbobenzoxy-L-alanine. Yield 94%. $[\alpha]_D=+16.3°$ (c=1.12, dichloromethane). m.p. 103–105°.

12d N-[2(N-Carbobenzoxy-L-valyl-glycyl)-amino-2-deoxy-β-D-glucopyranosyl]-N-tetradecyl-dodecanamide.
   from N-(2-glycyl-amino-2-deoxy-β-D-glucopyranosyl)-N-tetradecyl-dodecanamide and N-carbobenzoxy-L-valine. Yield 76%. $[\alpha]_D=+17.8°$ (c=1.09, dichloromethane). m.p. 85–86°.

12e N-[2-(N-Carbobenzoxy-L-seryl-glycyl)-amino-2-deoxy-β-D-glucopyranosyl]-N-tetradecyl-dodecanamide.
   from N-(2-glycyl-amino-2-deoxy-β-D-glucopyranosyl)-N-tetradecyl-dodecanamide and N-carbobenzoxy-L-serine. Yield 76%. $[\alpha]_D=+20.3°$ (c=0.89, dichloromethane). m.p. 87–89°.

12f N-[2-(N-Carbobenzoxy-O-benzyl-L-glutamyl-glycyl)-amino-2-deoxy-β-D-glucopyranosyl]-N-tetradecyl-dodecanamide.
   from N-(2-glycyl-amino-2-deoxy-β-D-glucopyranosyl)-N-tetradecyl-dodecanamide and N-carbobenzoxy-O-benzyl-L-glutamic acid.

12g N-[2-(N-Carbobenzoxy-L-glutaminyl-glycyl)-amino-2-deoxy-β-D-glucopyranosyl]-N-tetradecyl-dodecanamide.
   from N-(2-glycyl-amino-2-deoxy-β-D-glucopyranosyl)-N-tetradecyl-dodecanamide and N-carbobenzoxy-L-glutamine.

12h N-[2-(N-Carbobenzoxy-glycyl-glycyl-glycyl)-amino-2-deoxy-β-D-glucopyranosyl]-N-tetradecyl-dodecanamide.
   from N-(2-glycyl-amino-2-deoxy-β-D-glucopyranosyl)-N-tetradecyl-dodecanamide and N-cabobenzoxy-glycyl-glycine. Yield 52%. $[\alpha]_D=+14.7°$ (c=1.01, tetrahydrofuran). m.p. 99–100°.

12i N-[2-(N-Carbobenzoxy-glycyl-glycyl-glycyl-glycyl)-amino-2-deoxy-β-D-glucopyranosyl]-N-tetradecyl-dodecanamide.
   from N-(2-glycyl-amino-2-deoxy-β-D-glucopyranosyl)-N-tetradecyl-dodecanamide and N-carbobenzoxy-glycyl-glycyl-glycine.

12j N-[2-(N-Carbobenzoxy-L-alanyl-glycyl-glycyl)-amino-2-deoxy-β-D-glucopyranosyl]-N-tetradecyl-dodecanamide.
   from N-(2-glycyl-amino-2-deoxy-β-D-glucopyranosyl)-N-tetradecyl-dodecanamide and N-carbobenzoxy-L-alanyl-glycine.

12k N-[2-(N-Carbobenzoxy-L-alanyl-L-alanyl-glycyl)-amino-2-deoxy-β-D-glucopyranosyl]-N-tetradecyl-dodecanamide.
   from N-(2-glycyl-amino-2-deoxy-β-D-glucopyranosyl)-N-tetradecyl-dodecanamide and N-carbobenzoxy-L-alanyl-L-alanine. Yield 70%. $[\alpha]_D=+10.3°$ (c=0.92, tetrahydrofuran). m.p. 99–100°.

13a N-[2-(N-Carbobenzoxy-glycyl-glycyl)-amino-2-deoxy-β-D-glucopyranosyl]-N-octadecyl-dodecanamide.
   from N-(2-glycyl-amino-2-deoxy-β-D-glucopyranosyl)-N-octadecyl-dodecanamide and N-carbobenzoxy-glycine.

13b N-[2-(N-Carbobenzoxy-L-valyl-glycyl)-amino-2-deoxy-β-D-glucopyranosyl]-N-octadecyl-dodecanamide.
   from N-(2-glycyl-amino-2-deoxy-β-D-glucopyranosyl)-N-octadecyl-dodecanamide and N-carbobenzoxy-L-valine.

13c N-[2-(N-Carbobenzoxy-L-leucyl-glycyl)-amino-2-deoxy-β-D-glucopyranosyl]-N-octadecyl-dodecanamide.
   from N-(2-glycyl-amino-2-deoxy-β-D-glucopyranosyl)-N-octadecyl-dodecanamide and N-carbobenzoxy-L-leucine.

13d N-[-(N-Carbobenzoxy-O-benzyl-L-glutamyl-glycyl)-amino-2-deoxy-β-D-glucopyranosyl]-N-octadecyl-dodecanamide.
   from N-(2-glycyl-amino-2-deoxy-β-D-glucopyranosyl)-N-octadecyl-dodecanamide and N-carbobenzoxy-O-benzyl-L-glutamic acid.

13e N-[2-(N-Carbobenzoxy-L-glutaminyl-glycyl)-amino-2-deoxy-β-D-glucopyranosyl]-N-octadecyl-dodecanamide.
   from N-(2-glycyl-amino-2-deoxy-β-D-glucopyranosyl)-N-octadecyl-dodecanamide and N-carbobenzoxy-L-glutamine.

13f N-[2-(Tri-N-carbobenzoxy-L-arginyl-glycyl)-amino-2-deoxy-β-D-glucopyranosyl]-N-octadecyl-dodecanamide.
  from N-(2-glycyl-amino-2-deoxy-β-D-glucopyranosyl)-N-octadecyl-dodecanamide and tri-N-carbobenzoxy-L-arginine.
14a N-[2-(N-Carbobenzoxy-glycyl-glycyl)-amino-2-deoxy-β-D-glucopyranosyl]-N-tetradecyl-octadecanamide.
  from N-(2-glycyl-amino-2-deoxy-β-D-glucopyranosyl)-N-tetradecyl-octadecanamide and N-carbobenzoxy-glycine.
14b N-[2-(N-Carbobenzoxy-glycyl-L-alanyl)-amino-2-deoxy-β-D-glucopyranosyl]-N-tetradecyl-octadecanamide.
  from N-(2-L-alanyl-amino-2-deoxy-β-D-glucopyranosyl)-N-tetradecyl-octadecanamide and N-carbobenzoxy-glycine.
14c N-[2-(N-Carbobenzoxy-L-leucyl-L-alanyl)-amino-2-deoxy-β-D-glucopyranosyl]-N-tetradecyl-octadecanamide.
  from N-(2-L-alanyl-amino-2-deoxy-β-D-glucopyranosyl)-N-tetradecyl-octadecanamide and N-carbobenoxy-L-leucine.
14d N-[2-(N-Carbobenzoxy-L-alanyl-L-leucyl)-amino-2-deoxy-β-D-glucopyranosyl]-N-tetradecyl-ocadecanamide.
  from N-(2-L-leucyl-amino-2-deoxy-β-D-glucopyranosyl)-N-tetradecyl-octadecanamide and N-carbobenzoxy-L-alanine.
14e N-[2-N-Carbobenzoxy-L-leucyl-L-leucyl)-amino-2-deoxy-β-D-glucopyranosyl]-N-tetradecyl-octadecanamide.
  from N-(2-L-leucyl-amino-2-deoxy-β-D-glucopyranosyl)-N-tetradecyl-octadecanamide and N-carbobenzoxy-L-leucine. Yield 61%. $R_f$ 0.50 (dichloromethane/methanol/conc. ammonia 15:1:0.1).
15a N-[2-(N-Carbobenzoxy-glycyl-glycyl)-amino-2-deoxy-β-D-glucopyranosyl]-N-octadecyl-octadecanamide.
  from N-(2-glycyl-amino-2-deoxy-β-D-glucopyranosyl)-N-octadecyl-octadecanamide and N-carbobenzoxy-glycine.
15b N-[2-(N-Carbobenzoxy-L-alanyl-L-alanyl)-amino-2-deoxy-β-D-glucopyranosyl]-N-octadecyl-octadecanamide.
  from N-(2-amino-2-deoxy-β-D-glucopyranosyl)-N-octadecyl-tadecanamide and N-carbobenzoxy-L-alanyl-L-alanine.
15c N-[2-N-(Carbobenzoxy-D-alanyl-L-alanyl)-amino-2-deoxy-β-D-glucopyranosyl]-N-octadecyl-octadecanamide.
  from N-(2-amino-2-deoxy-β-D-glucopyranosyl)-N-octadecyl-octadecanamide and N-carbobenzoxy-D-alanyl-L-alanine.
15d N-[2-(N-Carbobenzoxy-D-alanyl-alanyl)-amino-2-deoxy-β-D-glucopyranosyl]-N-octadecyl-octadecanamide.
  from N-(2-amino-2-deoxy-β-D-glucopyranosyl)-N-octadecyl-octadecanamide and N-carbobenzoxy-D-alanyl-D-alanine.
15e N-[2-(N-Carbobenzoxy-D-alanyl-L-alanyl)-amino-2-deoxy-β-D-glucopyranosyl]-N-octadecyl-octadecanamide.
  from N-(2-amino-2-deoxy-β-D-glucopyranosyl)-N-octadecyl-octadecanamide and N-carbobenzoxy-D-alanyl-L-alanine.
15f N-[2-(DI-N-tert-butyloxycarbonyl-L-lysyl-L-alanyl)-amino-2-deoxy-β-D-glucopyranosyl]-N octadecyl-octadecanamide.
  from N-(2-amino-2-deoxy-β-D-glucopyranosyl)-N-octadecyl-octadecanamide and di-N-tert-butyloxycabonyl-L-lysyl-L-alanine.
16a N-[2-(N-tert-Butyloxycarbonyl-glycyl-glycyl)-amino-2-deoxy-β-D-glucopyranosyl]-N-tetradecyl-oleamide.
  from N-(2-glycyl-amino-2-deoxy-β-D-glucopyranosyl)-N-tetradecyl-olemide and N-tert-butyloxycarbonyl-glycine. Yield 68%. $[\alpha]_D=+14.5°$ (c=0.92, tetrahydrofuran).
16b N-[2-(N-tert-Butyloxycarbonyl-L-alanyl-glycyl)-amino-2-deoxy-β-D-glucopyranosyl]-N-tetradecyl-oleamide.
  from N-(2-glycyl-amino-2-deoxy-β-glucopyranosyl)-N-tetradecyl-oleamide and N-tert-butyloxycarbonyl-L-alanine. Yield 79%. $[\alpha]_D=+12.1°$ (c=0.87, tetrahydrofuran).
16c N-[2-(N-tert-Butyloxycarbonyl-glycyl-glycyl-glycyl)-amino-2-deoxy-β-D-glucopyranosyl]-N-tetradecyl-oleamde.
  from N-(2-glycyl-amino-2-deoxy-β-D-glucopyranosyl)-N-tetradecyl-oleamide and N-tert-butyloxycarbonyl-glycyl-glycine. Yield 74%. $[\alpha]_D=+14.2°$ (c=1.00, tetrahydrofuran).
16d N-[2-(N-tert-Butyloxycarbonyl-L-alanyl-L-alanyl-glycyl)-amino-2-deoxy-β-D-glucopyranosyl]-N-tetradecyl-oleamide.
  from N-(2-glycyl-amino-2-deoxy-β-D-glucopyranosyl)-N-tetradecyl-oleamide and N-tert-butyloxycarbonyl-L-alanyl-L-alanine. Yield 71%. $[\alpha]_D=+7.4°$ (c=0.82, tetrahydrofuran).
16e N-[2-(N-tert-Butyloxycarbonyl-glycyl-L-alanyl)-amino-2-deoxy-β-D-glucopyranosyl]-N-tetradecyl-oleamide.
  from N-(2-L-alanyl-amino-2-deoxy-β-D-glueopyranosyl)-N-tetradecyl-oleamide and N-tert-butloxycarbonyl-glycine. Yield 61%. $[\alpha]_D=+1.2°$ (c=0.86, tethydrofuran).
16f N-[2-(N-tert-Butyloxycarbonyl-L-alanyl-L-alanyl)-amino-2-deoxy-β-D-glucopyranosyl]-N-tetradecyl-oleamide.
  from N-(2-L-alanyl-amino-2-deoxy-β-D-glucopyranosyl)-N-tetradecyl-oleamide and N-tert-butyloxycarbonyl-L-alanine. Yield 59%. $[\alpha]_D=+0.2°$ (c=0.86, tetrahydrofuran).
16g N-[2-(N-tert-Butyloxycarbonyl-L-leucyl-L-alanyl)-amino-2-deoxy-β-D-glucopyranosyl]-N-tetradecyl-oleamide.
  from N-(2-L-alanyl-amino-2-deoxy-β-D-glucopyranosyl)-N-tetradecyl-oleamide and N-tert-butyloxycarbonyl-L-leucine. Yield 56%. $[\alpha]_D=-2.7°$ (c=0.86, tetrahydrofuran).
16h N-[2-(N-tert-Butyloxycarbonyl-glycyl-glycyl-L-alanyl)-amino-2-deoxy-β-D-glucopyranosyl]-N-tetradecyl-oleamide.
  from N-(2-L-alanyl-amino-2-deoxy-β-D-gluopyranosyl)-N-tetradecyl-oleamide and N-tert-butyloxycarbonyl-glycyl-glycine. Yield 56%. $[\alpha]_D=+8.5°$ (c=0.82, tetrahydrofuran).
16i N-[2-(N-tert-Butyloxycarbonyl-glycyl-L-leucyl)-amino-2-deoxy-β-D-glucopyranosyl]-N-tetradecyl-oleamide.
  from N-(2-L-leucyl-amino-2-deoxy-β-D-glucopyranosyl)-N-tetradecyl-oleamide and N-tert-butyloxycarbonyl-glycine. Yield 79%. $[\alpha]_D=-1.4°$ (c=0.87, tetrahydrofuran).
16j N-[2-(N-tert-Butyloxycarbonyl-L-alanyl-L-leucyl)-amino-2-deoxy-β-D-glucopyranosyl]-N-tetradecyl-oleamide.

from N-(2-L-leucyl-amino-2-deoxy-β-D-glucopyranosyl)-N-tetradecyl-oleamide and N-tert-butyloxycarbonyl-L-alanine. Yield 90%. [α]$_D$=−8.1° (c=0.98, tetrahydrofuran).

16k N-[2-(N-tert-Butyloxycarbonyl-glycyl-glycyl-L-leucyl)-amino-2-deoxy-β-D-glucopyranosyl]-N-tetradecyl-oleamide.

from N-(2-L-leucyl-amino-2-deoxy-β-D-glucopyranosyl)-N-tetradecyl-oleamide and N-tert-butyloxycarbonyl-glycyl-glycine. Yield 92%. [α]$_D$=+4.2° (c=0.83, tetrahydrofuran).

17a N-[2-(N-tert-Butyloxycarbonyl-glycyl-glycyl)-amino-2-deoxy-β-D-glucopyranosyl]-N-octadecyl-oleamide.

from N-(2-glycyl-amino-2-deoxy-β-D-glucopyranosyl)-N-octadecyl-oleamide and N-tert-butyloxycarbonyl-glycine. 17b N-[2-(N-tert-Butyloxycarbonyl-L-alanyl-glycyl)-amino-2-deoxy-β-D-glucopyranosyl]-N-octadecyl-oleamide.

from N-(2-glycyl-amino-2-deoxy-β-D-glucopyranosyl)-N-octadecyl-oleamide and N-tert-butyloxycarbonyl-L-alanine. 17c N-[2-(N-tert-Butyloxycarbonyl-O-tert-butyl-L-aspartyl-glycyl)-amino-2-deoxy-β-D-glucopyranosyl]-N-octadecyl-oleamide.

from N-(2-glycyl-amino-2-deoxy-β-D-glucopyranosyl)-N-octadecyl-olemide and N-tert-butyloxycarbonyl-O-tert-butyl-L-aspartic acid. Yield 88%. [α]$_D$= +13.8° (c=0.93, dichlorometane).

17d N-[2-(N-tert-Butyloxycarbonyl-glycyl-glycyl-glycyl)-amino-2-deoxy-β-D-glucopyranosyl]-N-octadecyl-oleamide.

from N-(2-glycyl-amino-2deoxy-β-D-glucopyranosyl)-N-octadecyl-oleamide and N-tert-butyloxycarbonyl-glycyl-gycine. Yield 81%. [α]$_D$=+15.0° (c=0.94, dichloromethane).

17e N-[2-(N-tert-Butyloxycarbonyl-L-alanyl-L-alanyl-glycyl)-amino-2-deoxy-β-D-glucopyranosyl]-N octadecyl-oleamide.

from N-(2-glycyl-amino-2-deoxy-β-D-glucopyranosyl)-N-octadecyl-oleamide and N-tert-butyloxycarbonyl-L-alanyl-L-alanine. Yield 55%. [α]$_D$=+10.3° (c=0.85, dichloromethane).

17f N-[2-(N-tert-Butyloxycarbonyl-glycyl-L-alanyl)-amino-2-deoxy-β-D-glucopyranosyl]-N-octadecyl-oleamide.

from N-(2-L-alanyl-amino-2-deoxy-β-D-glucopyranosyl)-N-octadecyl-oleamide and N-tert-butyloxycarbonyl-glycine.

17g N-[2-(N-tert-Butyloxycarbonyl-O-tert-butyl-L-aspartyl-L-alanyl)-amino-2-deoxy-β-D-glucopyranosyl]-N-octadecyl-oleamide.

from N-(2-L-alanyl-amino-2-deoxy-β-D-glucopyranosyl)-N-octadecyl-oleamide and N-tert-butyloxycarbonyl-O-tert-butyl-L-aspartic acid. Yield 27%. [α]$_D$=−1.5° (c=0.55, dichloromethane).

17h N-[2-(N-tert-Butyloxycarbonyl-glycyl-glycyl-L-alanyl)-amino-2-deoxy-β-D-glucopyranosyl]-N-octadecyl-oleamide.

from N-(2-L-alanyl-amino-2-deoxy-β-D-glucopyranosyl)-N-octadecyl-oleamide and N-tert-butyloxycnbonyl-glycyl-glycine. Yield 76%. [α]$_D$=+14.9° (c=1.05, dichloromethane).

17i N-[2-(N-tert-Butyloxycarbonyl-L-alanyl-L-alanyl-L-alanyl)-amino-2-deoxy-β-D-glucopyranosyl]-N-octadecyl-oleamide.

from N-(2-L-alanyl-amino-2-deoxy-β-D-glucopyranosyl)-N-otadecyl-oleamide and N-tert-butyloxycarbonyl-L-alanyl-L-alanine. Yield 75%. [α]$_D$=+17.9° (c=0.96, dichloromethane).

17j N-[2-(di-N-tert-Butyloxycarbonyl-L-lysyl-L-alanyl)-amino-2-deoxy-β-D-glucopyranosyl]-N-octadecyl-oleamide.

from N-(2-L-alanyl-amino-2-deoxy-β-D-glucopyranosyl)-N-octadecyl-oleamide and di-N-tert-butyloxycarbonyl-L-lysine. Yield 95%. [α]$_D$=−0.12° (c=0.84, dichloromethane).

18a N-[2-N-Carbobenzoxy-glycyl-glycyl)-amino-2-deoxy-β-D-galactopyranosyl]-N-dodecyl-octadecanamide.

from N-(2-glycyl-amino-2-deoxy-β-D-galactopyranosyl)-N-dodecyl-octadecanamide and N-carbobenzoxy-glycine.

18b N-[2-N-Carbobenzoxy-L-alanyl-glycyl)-amino-2-deoxy-β-D-galactopyranosyl]-N-dodecyl-octadecananmide.

from N-(2-glycyl-amino-2-deoxy-β-D-galactopyranosyl)-N-dodecyl-octadecanamide and N-carbobenzoxy-L-alanine.

Example 2

General procedure for reacting the N-protected 2-aminoacylamino-2-deoxy compounds, substituted with amino acids, of the formula (I) to give the N-unsubstituted 6-aminoacylamino-6-deoxy compound of the formula (I):

The N-carbobenzoxy-protected compound of the general formula (VI) (1.0 mmol) is dissolved in tetrahydrofuran (10 ml), methanol (5 ml) and 1N hydrochloric acid (1 ml), and 10% palladium on carbon (0.2 g) is added. The mixture is hydrogenated in a hydrogen atmosphere under atmospheric pressure for 16 h. The mixture is subsequently filtered over a Celite filter bed and the residue is concentrated under reduced pressure. In many cases crystallization proceds from methanol (4 ml) and conc. ammonia (0.2 ml). Otherwise, the residue is purified by column chromatography over silica gel (eluent dichloromethane/methanol/conc. ammonia 10:1:0.1). For conversion to the corresponding hydrochloride, the residue can be dissolved in tetrahydrofuran (5 ml), water (30 ml) and 1N hydrochloric aid (1.5 ml) and freeze-dried.

General procedure for eliminating the tert-butyloxycarbonyl groups in the compounds of the formula (I) to give the amines of the formula (I):

The compound of the general formula (VI) (1.0 mmol), substituted with the tert-butyloxycarbonyl group, is dissolved in dichloromethane (10 ml) at 0°, and trifluoroacetic acid (10 mnl) is added. After 2 h at 0°, the mixture is diluted with toluene (50 ml) and concentrated under reduced pressure. The residue obtained is taken up three times in toluene (50 ml each time) and in each case concentrated under reduced pressure. The residue obtained is purified by column chromatography over silica gel (gradient dichloromethane-methanol-conc. ammonia 20:1:0.1→10:1:0.1→10:3:0.1). For conversion to the corresponding hydrochloride, the residue can be dissolved in tetrahydrofuran (5 ml), water (30 ml) and 1N hydrochloric acid (1.5 ml) and freeze-dried.

21a N-(2-Glycyl-glycyl-amino-2-deoxy-β-D-glucopyranosyl)-N-dodecyl-dodecanamide.

21b N-(2-L-Alanyl-glycyl-amino-2-deoxy-β-D-glucopyranosyl)-N-dodecyl-dodecanamide.

21c N-(2-L-Phenylalanyl-glycyl-amino-2-deoxy-β-D-glucopyranosyl)-N-dodecyl-dodecanamide.

21d N-(2-Glycyl-L-alanyl-amino-2-deoxy-β-D-glucopyranosyl)-N-dodecyl-dodecanamide.

21e N-(2-Glycyl-D-alanyl-amino-2-deoxy-β-D-glucopyranosyl)-N-dodecyl-dodecanamide.

21f N-(2-L-Aspartyl-D-alanyl-amino-2-deoxy-β-D-glucopyranosyl)-N-dodecyl-dodecanamide.

22a N-(2-Glycyl-glycyl-amino-2-deoxy-β-D-glucopyranosyl)-N-tetradecyl-dodecanamide.
Yield 91%. $[\alpha]_D=+14.9°$ (c=0.84, N,N-dimethylformamide), m.p. 163° (decomposition).

22b N-(2-Sarcosyl-glycyl-amino-2-deoxy-β-D-glucopyranosyl)-N-tetradecyl-dodecanamide.
Yield 68%. $[\alpha]_D=+16.1°$ (c=0.93, N,N-dimethylformamide), m.p. 116°.

22c N-(2-L-Alanyl-glycyl-amino-2-deoxy-β-D-glucopyranosyl)-N-tetradecyl-dodecanamide.
Yield 90%. $[\alpha]_D=+18.7°$ (c=0.97, N,N-dimethylformamide), m.p. 115–117°.

22d N-(2-L-Valyl-glycyl-amino-2-deoxy-β-D-glucopyranosyl)-N-tetradecyl-dodecanamide.
Yield 90%. $[\alpha]_D=+44.7°$ (c=0.96, N,N-dimethylformamide), m.p. 120° (decomposition).

22e N-(2-L-Seryl-glycyl-amino-2-deoxy-β-D-glucopyranosyl)-N-tetradecyl-dodecanamide.
Yield 68%. $[\alpha]_D=+11.3°$ (c=0.98, N,N-dimethylformamide), m.p. 141–143°.

22f N-(2-L-Glutamyl-glycyl-amino-2-deoxy-β-D-glucopyranosyl)-N-tetradecyl-dodecanamide.

22g N-(2-L-Glutaminyl-glycyl-amino-2-deoxy-β-D-glucopyranosyl)-N-tetradecyl-dodecanamide.

22h N-(2-L-Glycyl-glycyl-glycyl-amino-2-deoxy-β-D-glucopyranosyl)-N-tetradecyl-dodecanamide.
Yield 78%. $[\alpha]_D=+17.1°$ (c=0.92, N,N-dimethylformamide), m.p. 177–178°.

22i N-(2-Glycyl-glycyl-glycyl-glycyl-amino-2-deoxy-β-D-glucopyranosyl)-N-tetradecyl-dodecanamide.

22j N-(2-Alanyl-glycyl-glycyl-amino-2-deoxy-β-D-glucopyranosyl)-N-tetradecyl-dodecanamide.

22k N-(2-L-Alanyl-L-alanyl-glycyl-amino-2-deoxy-β-D-glucopyranosyl)-N-tetradecyl-dodecanamide.
Yield 80%. $[\alpha]_D=+21.1°$ (c=0.90, N,N-dimethylformamide), m.p. 132–134°.

23a N-(2-Glycyl-glycyl-amino-2-deoxy-β-D-glucopyranosyl)-N-octadecyl-dodecanamide.

23b N-(2-L-Valyl-glycyl-amino-2-deoxy-β-D-glucopyranosyl)-N-octadecyl-dodecanamide.

23c N-(2-L-Leucyl-glycyl-amino-2-deoxy-β-D-glucopyranosyl)-octadecyl-dodecanamide.

23d N-(2-L-Glutamyl-glycyl-amino-2-deoxy-β-D-glucopyranosyl)-N-octadecyl-dodecanamide.

23e N-(2-L-Glutaminyl-glycyl-amino-2-deoxy-β-D-glucopyranosyl)-N-octadecyl-dodecanamide.

23f N-(2-L-Arginyl-glycyl-amino-2-deoxy-β-D-glucopyranosyl)-N-octadecyl-dodecanamide.

24a N-(2-Glycyl-glycyl-amino-2-deoxy-β-D-glucopyranosyl)-N-tetradecyl-octadecanamide.

24b N-(2-Glycyl-L-alanyl-amino-2-deoxy-β-D-glucopyranosyl)-N-tetradecyl-octadecanamide.

24c N-(2-L-Leucyl-L-alanyl-amino-2-deoxy-β-D-glucopyranosyl)N-tetradecyl-octadecanamide.

24d N-(2-L-Alanyl-L-leucyl-amino-2-deoxy-β-D-glucopyranosyl)-N-tetradecyl-octadecanamide.

24e N-(2-L-Leucyl-L-leucyl-amino-2-deoxy-β-D-glucopyranosyl)-N-tetradecyl-octadecanamide.

25a N-(2-Glycyl-glycyl-amino-2-deoxy-β-D-glucopyranosyl)-N-octadecyl-octadecanamide.

25b N-(2-L-Alanyl-L-alanyl-amino-2-deoxy-β-D-glucopyranosyl)-N-octadecyl-octadecanamide.

25c N-(2-D-Alanyl-L-alanyl-amino-2-deoxy-β-D-glucopyranosyl)-N-octadecyl-octadecanamide.

25d N-(2-D-Alanyl-D-alanyl-amino-2-deoxy-β-D-glucopyranosyl)-N-octadecyl-octadecanamide.

25e N-(2-D-Alanyl-L-alanyl-amino-2-deoxy-β-D-glucopyranosyl)-N-octadecyl-octadecanamide.

25f N-(2-L-Lysyl-L-alanyl-amino-2-deoxy-β-D-glucopyranosyl)-N-octadecyl-octadecanamide.

26a N-(2-Gycyl-gycyl-amino-2-deoxy-β-D-glucopyranosyl)-N-tetradecyl-oleamide.
Yield: 96%. $[\alpha]_D=+13.2°$ (c=0.86, tetrahydrofuran).

26b N-(2-L-Alanyl-glycyl-amino-2-deoxy-β-D-glucopyranosyl)-N-tetradecyl-oleamide.
Yield: 97%. $[\alpha]_D=+29.6°$ (c=0.90, tetrahydrofuran).

26c N-(2-Glycyl-glycyl-glycyl-amino-2-deoxy-β-D-glucopyranosyl)-N-tetradecyl-oleamide.
Yield: 86%. $[\alpha]_D=+13.1°$ (c=0.94, tetrahydrofuran).

26d N-(2-L-Alanyl-L-alanyl-glycyl-amino-2-deoxy-β-D-glucopyranosyl)-N-tetradecyl-oleamide.
Yield: 97%. $[\alpha]_D=+19.9°$ (c=0.87, tetrahydrofuran).

26e N-(2-Glycyl-L-alanyl-amino-2-deoxy-β-D-glucopyranosyl)-N-tetradecyl-oleamide.
Yield: 97%. $[\alpha]_D=-6.6°$ (c=1.05, tetrahydrofuran).

26f N-(2-L-Alanyl-L-alanyl-amino-2-deoxy-β-D-glucopyranosyl)-N-tetradecyl-oleamide.
Yield 98%. $[\alpha]_D=+7.1°$ (c=0.87, tetrahydrofuran).

26g N-(2-L-Leucyl-L-alanyl-amino-2-deoxy-β-D-glucopyranosyl)-N-tetradecyl-oleamide.
Yield: 96%. $[\alpha]_D=-1.6°$ (c=0.88, tetrahydrofuran).

26h N-(2-Glycyl-glycyl-L-alanyl-amino-2-deoxy-β-D-glucopyranosyl)-N-tetradecyl-oleamide.
Yield: 96%. $[\alpha]_D=+8.1°$ (c=0.97, tetrahydrofuran).

26i N-(2-Glycyl-L-leucyl-amino-2-deoxy-β-D-glucopyranosyl)-N-tetradecyl-oleamide.
Yield: 97%. $[\alpha]_D=-9.1°$ (c=1.02, tetrahydrofuran).

26j N-(2-L-Alanyl-L-leucyl-amino-2-deoxy-β-D-glucopyranosyl)-N-tetradecyl-oleamide.
Yield: 87%. $[\alpha]_D=+1.0°$ (c=0.74, tetrahydrofuran).

26k N-(2-Gycyl-glycyl-L-leucyl-amino-2-deoxy-β-D-glucopyranosyl)-N-tetradecyl-oleamide.
Yield: 95%. $[\alpha]_D=-2.9°$ (c=0.87, tetrahydrofuan).

27a N-(2-Glycyl-glycyl-amino-2-deoxy-β-D-glucopyranosyl)-N-octadecyl-oleamde.

27b N-(2-L-Alanyl-glycyl-amino-2-deoxy-β-D-glucopyranosyl)-N-octadecyl-oleamide.

27c N-(2-L-Aspartyl-glycyl-amino-2-deoxy-β-D-glucopyranosyl)-N-octadecyl-oleamide.
Yield 92%. $[\alpha]_D=+11.3°$ (c=0.90, N,N-dimethylformamide).

27d N-(2-Glycyl-glycyl-glycyl-amino-2-deoxy-β-D-glucopyranosyl)-N-octadecyl-oleamide.
Yield 94%. $[\alpha]_D=+12.5°$ (c=0.93, methanol).

27e N-(2-L-Alanyl-L-alanyl-glycyl-amino-2-deoxy-β-D-glucopyranosyl)-N-octadecyl-oleamide.
Yield 91%. $[\alpha]_D=+14.3°$ (c=0.92, methanol).

27f N-(2-Glycyl-L-alanyl-amino-2-deoxy-β-D-glucopyranosyl)-N-octadecyl-oleamide.

27g N-(2-L-Aspartyl-L-alanyl-amino-2-deoxy-β-D-glucopyranosyl)-N-octadecyl-oleamide.
Yield 88%. $[\alpha]_D=+35.6°$ (c=0.76, dichloromethane).

27h N-(2-L-Glycyl-glycyl-L-alanyl-amino-2-deoxy-β-D-glucopyranosyl)-N-octadecyl-oleamide.

Yield 96%. $[\alpha]_D=-57.1°$ (c=0.77, dichloromethane).

27i N-(2-L-Alanyl-L-alanyl-L-alanyl-amino-2-deoxy-β-D-glucopyranosyl)-N-octadecyl-oleamide.

Yield 85%. $[\alpha]_D=+7.4°$ (c=0.82, dichloromethane).

27j N-(2-L-Lysyl-L-alanyl-amino-2-deoxy-β-D-glucopyranosyl)-N-octadecyl-oleamide.

Yield 84%. $[\alpha]_D=+4.6°$ (c=1.09, methanol).

28a N-(2-Glycyl-glycyl-amino-2-deoxy-β-D-galactopyranosyl)-N-dodecyl-octadecanamide.

28b N-(2-L-Alanyl-glycyl-amino-2-deoxy-β-D-galactopyranosyl)-N-dodecyl-octadecanamide.

We claim:

1. (2-Aminoacylamino-2-deoxy-glycosyl)-amides substituted by amino acids, of the formula (I)

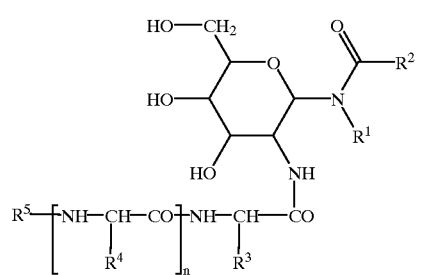

in which $R^1$ represents straight-chain or branched, saturated or unsaturated alkyl having up to 25 carbon atoms, $R^2$ represents straight-chain or branched, satuated or unsaturated alkyl having up to 25 carbon atoms, $R^3$ represents hydrogen, $C_1$- to $C_7$-alkyl, hydroxy-methyl, 1-hydroxy-ethyl, mercapto-methyl, 2-methylthio-ethyl, 3-amino-propyl, 3-ureido-propyl, 3-guanidyl-propyl, 4-amino-butyl, carboxy-methyl, carbamoyl-methyl, 2-carboxy-ethyl, 2-carbamoyl-ethyl, benzyl, 4-hydroxy-benzyl, 3-indolyl-methyl or 4-imidazolyl-methyl, $R^4$ has the above-indicated meaning of $R^3$ and is identical to or different from $R^3$, $R^5$ represents hydrogen or a protecting group which is customary in peptide chemistry, and in which n denotes a number 1, 2 or 3, and in the case where n=2 or 3 the individual meanings of $R^4$ are the same or different.

2. Compounds of the formula (I) according to claim 1 in which $R^1$ represents a straight-chain, saturated or monounsaturated alkyl radical having 10 to 20 carbon atoms, $R^2$ represents a straight-chain, saturated or monounsaturated alkyl radical having 10 to 20 carbon atoms, $R^3$ represents hydrogen, $C_1$- to $C_7$-alkyl, hydroxy-methyl, 1-hydroxy-ethyl, mercapto-methyl, 2-methylthio-ethyl, 3-amino-propyl, 3-ureido-propyl, 3-guanidyl-propyl, 4amino-butyl, carboxy-methyl, carbamoyl-methyl, 2-carboxy-ethyl, 2-carbamoyl-ethyl, benzyl, 4hydroxy-benzyl, 3-indolyl-methyl or 4imidazolyl-methyl, $R^4$ has the above-indicated meaning of $R^3$ and is identical to or different from $R^3$, $R^5$ represents hydrogen, acetyl, benzoyl, trichloroacetyl, trifluoroacetyl, methoxycarbonyl, tert-butyloxycarbonyl, allyloxycarbonyl, trichloroethoxycarbonyl, benzyloxycarbonyl or fluorenylmethoxycarbonyl, and in which n denotes a number 1, 2 or 3, and in the case where n=2 or 3 the individual meanings of $R^4$ are the same or different.

3. A method of stimulating the immune system of a human or animal which comprises administering to such human or animal an amount effective therefor of a compound according to claim 1.

4. A composition for stimulating the immune system of a human or animal comprising a compound according to claim 1 and a pharmaceutically acceptable carrier.

5. Process for the preparation of the compounds of the formula (I) according to claim 1, wherein a) N-(2-aminoacylamino-2-deoxy-hexopyranosyl)-N-alkyl carboxamides of the formula (II)

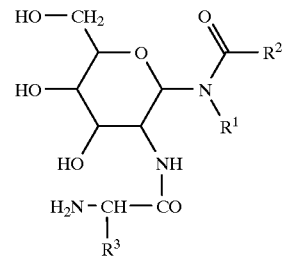

in which $R^1$, $R^2$ and $R^3$ are reacted with amino acid derivatives or di- or tripeptide derivatives of the formula (III)

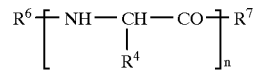

in which $R^6$ represents a protecting group, customary in peptide chemistry, for the nitrogen atom of amino acids, which can be eliminated while maintaining the peptide linkage, and $R^7$ represents a hydroxyl group or a leaving group, customary in peptide chemistry, for the activation of amino acids, n denotes a number 1, 2 or 3, and in the case where n is 2 or 3 the individual meanings of $R^4$ are the same or different;

with one another in such a way that an amide linkage is formed and compounds of the formula (I) are obtained and b) subsequently the amino-protecting groups $R^6$ are eliminated to give compounds having an unsubstituted amino groups, of the formula (I).

6. Process for the preparation of compounds of the formula (I) according to claim 1, wherein a) compounds of the formula (IV)

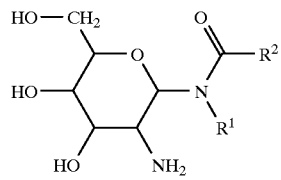
(IV)

in which
$R^1$ and $R^2$ are reacted with derivatives of di-, tri- or tetrapeptides of the formula (III)

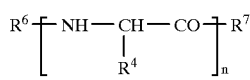
(III)

in which $R^6$ denotes a protecting group $R^7$ represents a hydroxyl group or a leaving group, customary in peptide chemistry, for the activation of amino acids n denotes a number 2, 3 or 4 and individual meanings of $R^4$ are the same or different with one another under the abovementioned conditions with formation of a peptide linkage, to give the compounds of the formula (V)

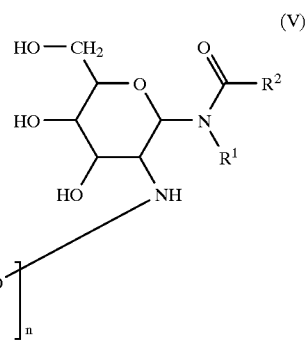
(V)

in which
$R^6$ represents a protecting group, customary in peptide chemistry, for the nitrogen atom of amino acids, which can be eliminated while maintaining the peptide linkage, and n denotes a number 2, 3 or 4 which are substituted on the N-terminal amino group, and b) subsequently the amino-protecting groups $R^6$ are eliminated to give compounds having an unsubstituted amino group, of the formula (I).

7. Process for the preparation of the compounds of the formula (I) according to claim 5, wherein
$R^1$ represents a straight-chain, saturated or monounsaturated alkyl radical having 10 to 20 carbon atoms.

8. Process for the preparation of the compounds of the formula (I) according to claim 5, wherein
$R^2$ represents a straight-chain, saturated or monounsaturated alkyl radical having 10 to 20 carbon atoms.

9. Process for the preparation of the compounds of the formula (I) according to claim 6, wherein
$R^1$ represents a straight-chain, saturated or monounsaturated alkyl radical having 10 to 20 carbon atoms.

10. Process for the preparation of the compounds of the formula (I) according to claim 6, wherein
$R^2$ represents a straight-chain, saturated or monounsaturated alkyl radical having 10 to 20 carbon atoms.

* * * * *

UNITED STATES PATENT AND TRADEMARK OFFICE
CERTIFICATE OF CORRECTION

PATENT NO.  : 5,905,071
DATED       : May 18, 1999
INVENTOR(S) : Lockhoff, et al.

It is certified that error appears in the above-identified patent and that said Letters Patent are hereby corrected as shown below:

| | |
|---|---|
| Title Page | U.S. PATENT DOCUMENTS: After "4,855,283, 8/1989, Lockhoff et al." insert --514/25-- |
| Col. 15, Line 33 | Delete "satuated" and substitue --saturated-- |
| Col. 15, Line 61 | Delete "4amino-butyl" and substitute --4-amino-butyl-- |
| Col. 15, Lines 62-63 | Delete "4hydroxy-benzyl" and substitute -- 4-hydroxy-benzyl -- |
| Col. 15, Line 63 | Delete "4imidazolyl-methyl" and substitue -- 4-imidazolyl-methyl -- |

Signed and Sealed this

Twenty-fifth Day of January, 2000

Attest:

*Attesting Officer*

*Acting Commissioner of Patents and Trademarks*